Figure 1:
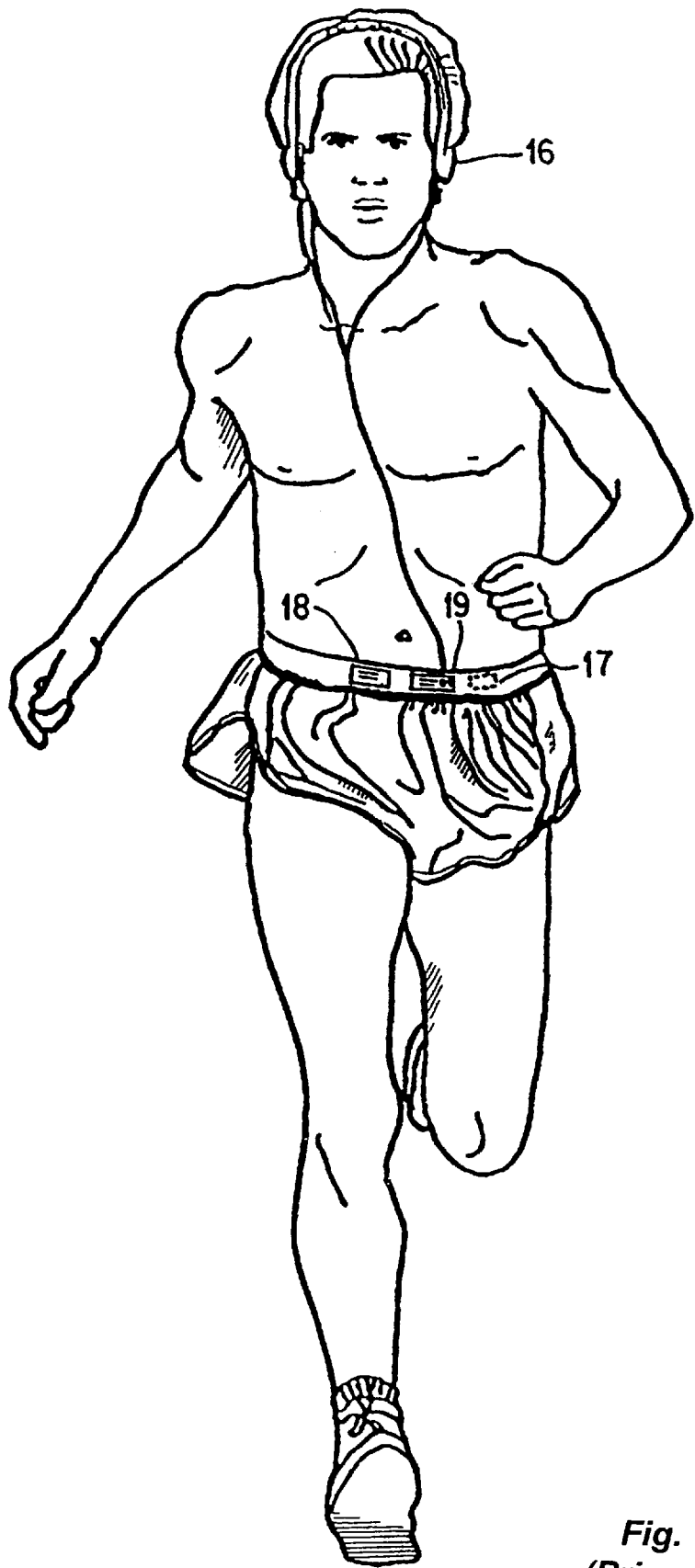

United States Patent [19]
Thorgersen

[11] Patent Number: 6,080,110
[45] Date of Patent: Jun. 27, 2000

[54] HEARTBEAT MONITOR FOR WEARING DURING EXERCISE

[75] Inventor: Harold Thorgersen, Woodbury, Conn.

[73] Assignee: Tel, Inc., Woodbury, Conn.

[21] Appl. No.: 09/293,903

[22] Filed: Apr. 19, 1999

[51] Int. Cl.[7] .................................................. A61B 5/00
[52] U.S. Cl. ........................ 600/500; 600/503; 600/322
[58] Field of Search ............................ 600/322–4, 500–3

[56] References Cited

U.S. PATENT DOCUMENTS

| | | | |
|---|---|---|---|
| 4,281,663 | 8/1981 | Pringle | 128/689 |
| 4,301,808 | 11/1981 | Taus | 128/687 |
| 4,334,544 | 6/1982 | Hill et al. | 128/664 |
| 4,434,801 | 3/1984 | Jiminez et al. | 128/689 |
| 4,867,442 | 9/1989 | Matthews | 272/93 |
| 5,179,951 | 1/1993 | Knudson | 600/322 |
| 5,213,099 | 5/1993 | Tripp, Jr. | 600/324 |
| 5,314,389 | 5/1994 | Dotan | 482/3 |
| 5,823,966 | 10/1998 | Buchert | 600/473 |

*Primary Examiner*—Robert L. Nasser
*Attorney, Agent, or Firm*—William C. Crutcher

[57] ABSTRACT

A heartbeat monitor for wearing during exercise and receiving audio heartbeat information includes a pulse rate detector having an infrared source and an infrared sensor on a flexible cup-shaped ear piece which fits into the ear canal.

5 Claims, 3 Drawing Sheets

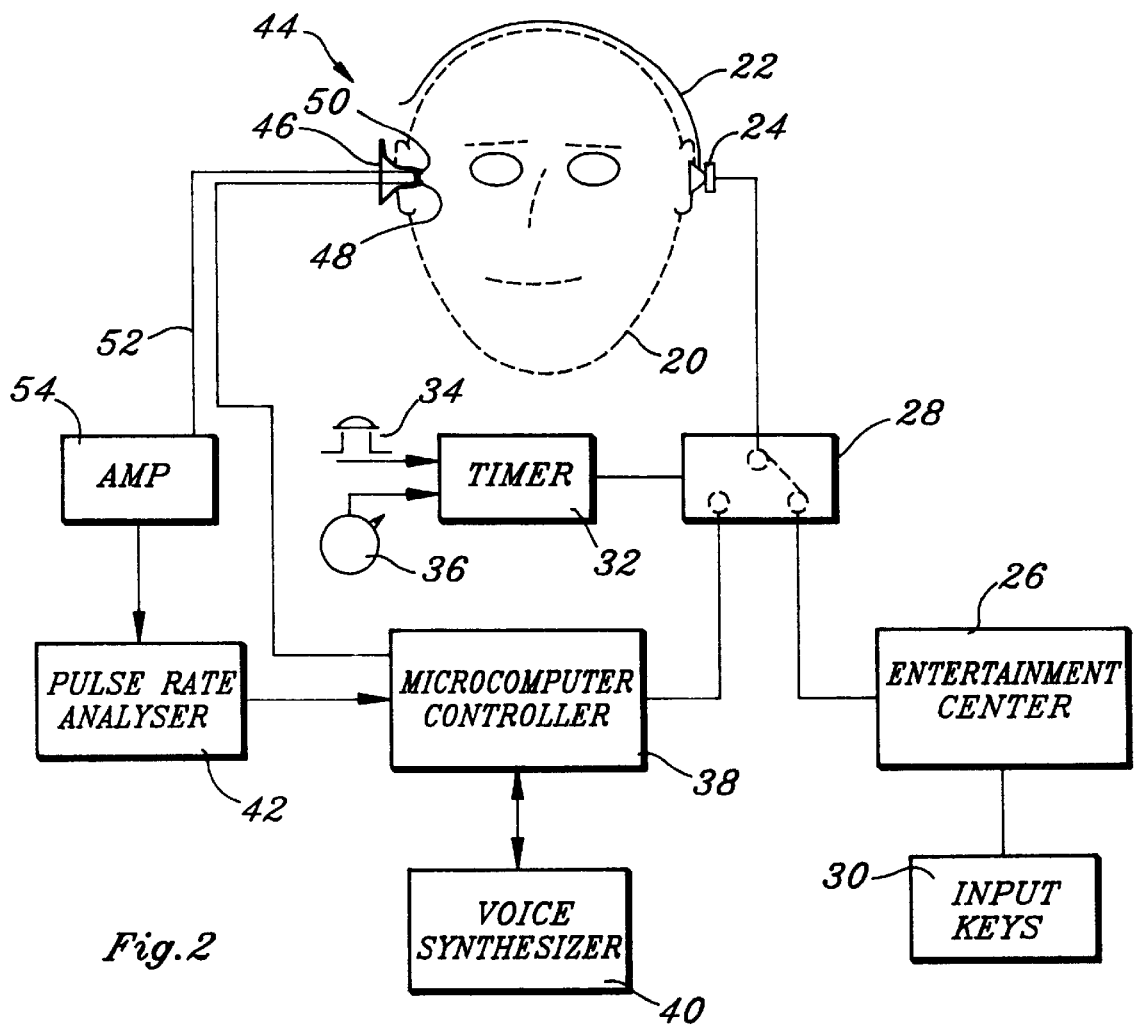
Fig. 2
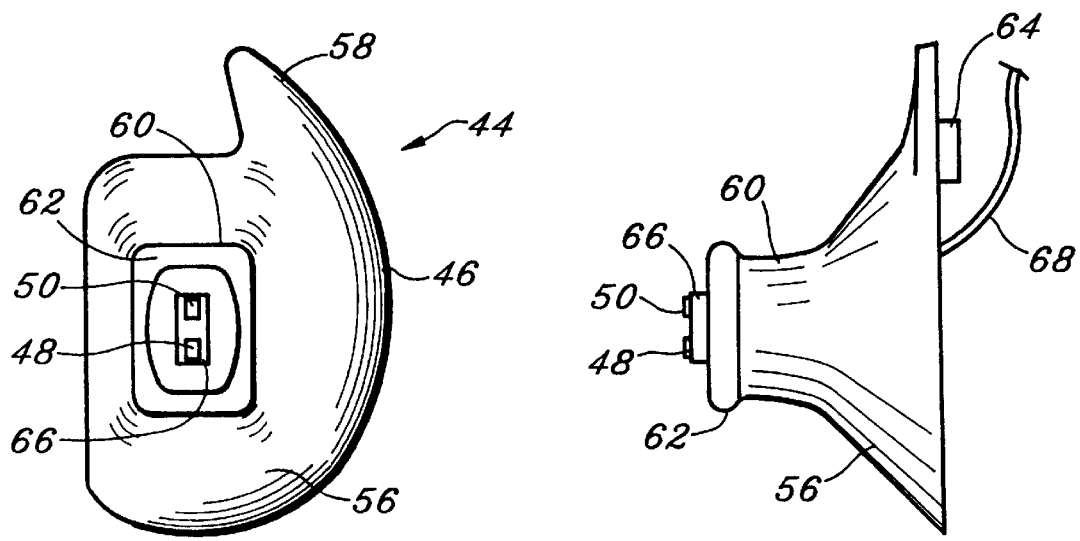
Fig. 3
Fig. 4

HEARTBEAT MONITOR FOR WEARING DURING EXERCISE

This invention relates generally to an improved heartbeat monitor for wearing during exercise, and more particularly to an improved pulse rate detector for such a heartbeat monitor.

A number of heartbeat monitors have been developed for detecting and displaying the heartbeat of a subject while exercising or performing other activities. Very elaborate electronic systems have been devised for receiving and analyzing a signal from a pulse rate detector, which is externally attached to the body. One such system is shown in U.S. Pat. No. 4,281,663—Pringle issued May 21, 1979. The usefulness of such systems depends upon the accuracy of the pulse rate detector and the degree to which the detector intrudes upon and interferes with the athletic activities of the person wearing the heart beat monitor. U.S. Pat. No. 4,867,442—Matthews also suggested the addition of a speech synthesizer to provide voice input to inform the user of the heartbeat rate so that it is unnecessary to view a display.

There are several techniques for detecting pulse rate using an external non-invasive detector. One type of pulse rate detector is an electrocardiograph (ECG). This device requires two electrodes to be in contact with the body of the user. Examples of these are seen in U.S. Pat. No. 5,314,389—Dotan issued May 24, 1994 and U.S. Pat. No. 4,434,801—Jiminez et al. issued Mar. 6, 1984. Dotan shows an ECG unit with one electrode forming part of an earphone and the other electrode either attached at the waist or to a strap on the chest. Dotan also discloses a radio or tape recorder with means for dimming the output of the radio or tape while a pulse rate is announced at predetermined intervals.

Another type of pulse rate monitor uses infrared (IR) devices to sense variations in emissivity, reflectivity or opacity of human tissue as the blood flow through the tissue changes with pulse rate. The IR device may simply be a photosensitive transistor or resistor which acts as a sensor to detect changes in infrared radiation naturally emitted by the human body. Or the sensor may be combined with an LED light source emitting light in the IR spectrum and forming a source/sensor pair. The source/sensor pair may either operate in the reflective mode or in the transmissive mode. In the reflective mode, both the source and the sensor are located on the same side of human tissue carrying a pulsating blood flow. In the transmissive mode the source and sensor are disposed on opposite sides of tissue or membrane and infrared is transmitted through the tissue.

An exercise unit involving infrared devices both of the reflective and of the transmissive types is shown in U.S. Pat. No. 4,301,808—Taus issued Nov. 19, 1979. In the Taus patent, the IR source and sensor units are located on the outer upper ear flap. U.S. Pat. No. 4,334,544—Hill issued Jun. 15, 1982 shows a transmissive IR source/sensor pair designed for attachment on opposite sides of the ear lobe with a spring clip.

All of the foregoing pulse rate detector systems require external electrodes with wiring to different parts of the body in the case of ECG units, or potentially uncomfortable external attachments in the case of IR transmissive devices which can interfere with movements of the body. Also external attachments or external electrodes are prone to receiving spurious signals or being knocked off or detached during exercise.

U.S. Pat. No. 5,823,966—Buchert issued Oct. 20, 1998 shows a single IR sensor inserted into the ear canal for detecting the infrared radiation naturally emitted. This device is designed for correlation with the blood concentration for measuring glucose levels making use of special characteristics of naturally occurring human infrared radiation from the tympanic membrane.

It would be desirable to have an improved non-invasive pulse rate detector for measuring heartbeat to be used in a heartbeat monitor for wearing during exercise. It would also be desirable to integrate such a detector with means to provide an audible indication of heartbeat rate during exercise.

Accordingly, one object of the present invention is to provide an improved sensor for a heartbeat monitor for wearing during exercise.

Still another object of the invention is to provide an improved IR pulse rate detector for wearing comfortably in the ear by a user during exercise.

Yet another object of the invention is to provide an improved pulse rate detector which is integrated with the headset for an audio system for hearing both pulse rate and audio entertainment during exercise.

SUMMARY OF THE INVENTION

Briefly stated the invention comprises an improved heartbeat monitor for wearing by a user during exercise, the monitor being of the type comprising a microcomputer controller, a pulse rate analyzer connected to receive an electrical pulse-rate signal and to output a voice command signal corresponding to the heartbeat rate of the user, a voice synthesizer providing a set of stored audio output signals corresponding to values assigned to a set of stored voice command signals, the microcomputer controller being programmed to receive a voice command signal from the pulse rate analyzer, to supply the voice command signal to the voice synthesizer and to output an audio signal corresponding to the pulse rate, and a headset having speaker means adapted to be held in proximity to at least one ear of the user and connected to receive the output audio signal, whereby a voice message indicating heartbeat rate may be selectively heard through the user's speaker means. The improvement comprises a pulse rate detector having an infrared source and an infrared sensor combined in a source/sensor pair on an ear piece adapted to fit into an ear canal of the user, the infrared source being periodically actuated by the microcomputer controller to illuminate the ear canal and cause IR radiation to be variably reflected to the infrared sensor to provide an electrical pulse-rate signal responsive to the user's heartbeat rate.

Preferably the pulse rate detector includes an ear piece having a projecting portion fitting within the ear canal with the source/sensor pair disposed on the end of the projecting portion. Preferably the ear piece comprises a flexible cup arranged to be supported by portions of the outer ear.

DRAWINGS

Figure 5:
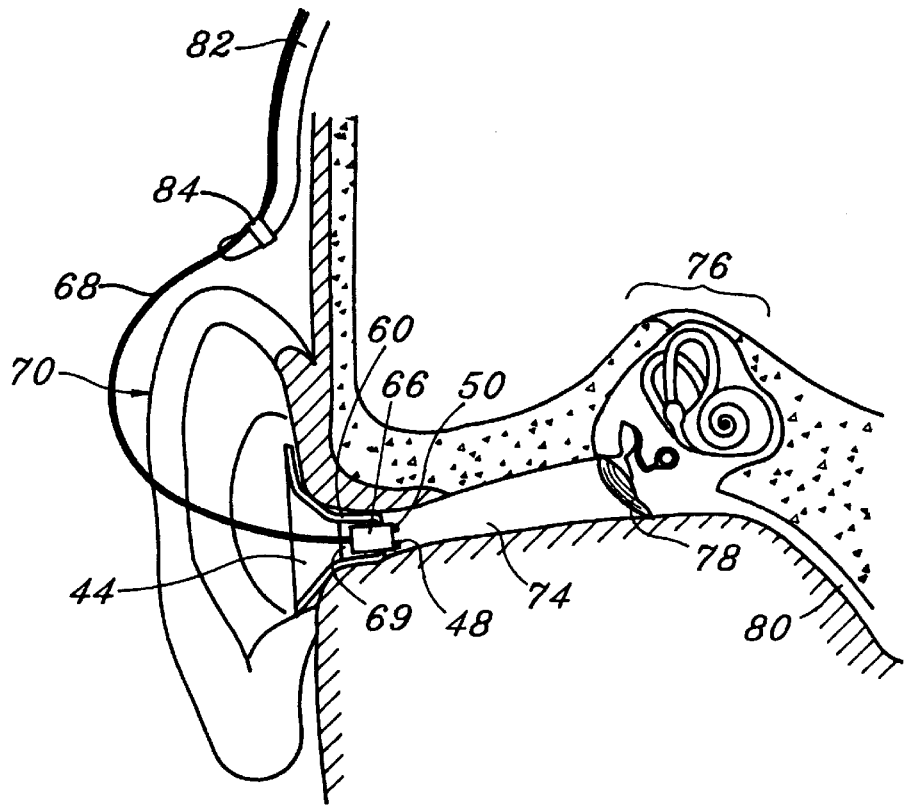
Figure 6:
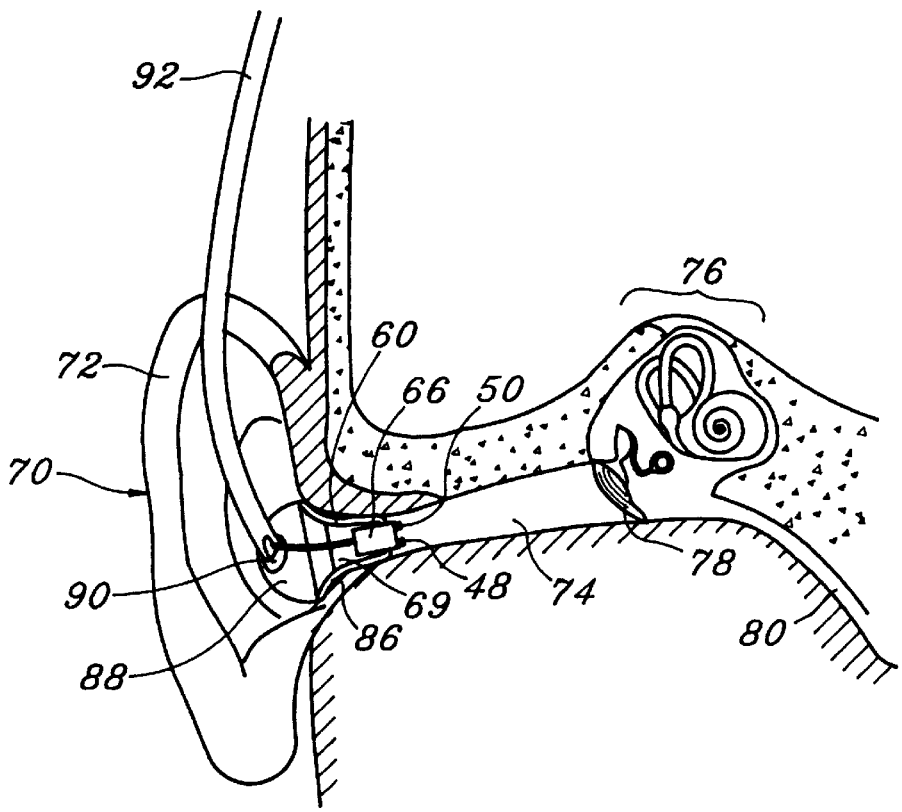

The invention will be more clearly understood by reference to the following description, taken in connection with the accompanying drawings, in which:

FIG. 1 is a front elevation view of a user wearing a heartbeat monitor during exercise according to the prior art, FIG. 2 is a simplified schematic block diagram illustrating the heartbeat monitor of the present invention, FIG. 3 is a top plan view of a pulse rate detector for insertion into the ear canal according to the present invention, FIG. 4 is a side elevation view of the pulse rate detector shown in FIG. 3, FIG. 5 is a cross-sectional view through a portion of a human ear illustrating placement of the preferred embodiment shown in FIGS. 3 and 4, and FIG. 6 is a cross-sectional view similar to FIG. 5, illustrating a modification of the present invention.

Referring now to FIG. 1, a prior art heartbeat monitor is shown as taken from

FIG. 1 of U.S. Pat. No. 5,314,389—Dotan issued May 24, 1994. A device is shown which provides an exercising person information at any desired period of time about his pulse rate. The information is given as vocal information with means for dimming the output of a radio or tape worn by the runner while a pulse rate is announced at predetermined intervals.

As shown in FIG. 1, the system comprises of an ECG apparatus 19, provided with electrode means 17, 16 at the waist level and as part of the earphone 16; a radio tape 18, provided with power source (battery or rechargeable batteries), a receiver 19 of the ECG signal containing control means, earphones 16 which are used to convey the vocal message to the jogger and as the second electrode.

Referring to FIG. 2 illustrating the present invention, a user 20 is provided with a headset 22 carrying a speaker 24 held in proximity with one ear of the user. An electronic entertainment center 26, such as a tape recorder, radio or solid state multimedia player outputs audio entertainment signals through a switch 28 in accordance with entertainment selections controlled by input keys 30. Switch 28 represents a solid state switch controlled by a timer 32. Timer 32 may be by-passed on demand from a manual pushbutton 34 operable by the user, but it is intended to re-cycle and provide an output at selectable intervals set by selector 36. A heartbeat rate audio signal to switch 28 is input from a microcomputer controller 38 as will be later described. Microcomputer controller 38 is also connected to a voice synthesizer 40 and a pulse rate analyzer 42.

In accordance with the present invention, a pulse rate detector shown generally as 44 comprises an ear piece 46 carrying an LED source 48 arranged to emit infrared radiation and an IR sensor 50 arranged to receive IR radiation reflected from source 48 within the ear canal. For example, source 48 could comprise an AlGaAs LED or a GaAs:Si LED emitting IR radiation in the 850–1000 nanometer region. Sensor 50 could be a phototransistor or photodiode. Many types of source/sensor pairs are commercially available in miniature integrated circuit packages.

Sensor 50 provides an electrical pulse-rate signal over line 52 to an amplifier 54. The amplified signal is supplied to the pulse rate analyzer 42, where it is analyzed and converted to a voice command signal and supplied to microcomputer controller 38.

Referring now to FIGS. 3 and 4 of the drawing, a preferred pulse rate detector 44 in accordance with the present invention, comprises an ear piece 46 on which are disposed an infrared LED source 48 and an infrared sensor 50 disposed in close proximity to one another. Ear piece 46 comprises a flexible plastic cup 56 which is hollow on the inside and contoured on its outer periphery 58 to fit inside the folds of the outer ear. Ear piece 46 includes a projecting portion 60 of the proper size to enter the ear canal, with an enlarged end portion 62 which will lodge in the ear canal and seal off light entry. Cup portion 56 is provided with a tab 64 to assist in removing the ear piece 46 and its projecting portion 60 from the ear canal. IR source 48 and IR sensor 50 are encased together in an integrated circuit package 66. The signal leads and common lead from the source/sensor pair are encased in a single insulated sheath 68 leading from the inside of cup 56. The IC package 66 for the source/sensor pair extends through the top of projecting portion 60 and is held within the upper end of cup 56 by a suitable elastomeric sealant.

Referring now to FIG. 5 of the drawing, the preferred ear piece 44 is illustrated as placed in an ear 70 of the user. Ear 70 is composed of outer ear 72, ear canal 74, inner ear 76, ear drum 78, and eustachian tube 80. Projecting portion 60 of ear piece 44 is positioned in the ear canal 74 with the IR source 48 and IR sensor 50 directed toward inner ear 76 and ear drum 78. The outer peripheral walls of the flexible cup flex to conform to the contours of the outer ear 72 and are held in position by portions of the outer ear. Tab 64 may be used for removal.

The headset 22 carrying a speaker 24 in the other ear of the user (see FIG. 2) includes a terminating headset portion 82. Sheath 68 containing the leads from the sensor/source pair is attached to terminating portion 82 of the headset by a clip 84, and from there is conducted to the other side of the headset to be consolidated with the normal leads from speaker 24. A single sheath of conductors may be led to the heartbeat monitor which preferably is mounted on the belt of the user in a manner similar to that shown in FIG. 1 of the prior art.

FIG. 6 illustrates an alternate form of the invention, in which an ear piece is held in place directly by the headset. Referring to FIG. 6 of the drawing, an ear piece 86 is illustrated which is shown in cross section to be constructed in the same manner as the ear piece 44. However rather than having lateral flexible walls, which are held in place by portions of the outer ear, the open end of the cup-shaped ear piece is provided with a closure member 88 having a pivotable connection 90. A terminating end 92 of the headset is connected by pivotable connector 90 to the closure piece 88, so the headset directly holds the ear piece 86 inside the ear canal 74.

OPERATION

Operation of the overall system will first be described by reference to the block diagram of FIG. 2. When the heartbeat monitor is not active, speaker 24 is connected through switch 28 to entertainment center 26 where an audio entertainment signal selected by input keys 30 is heard by user 20. At predetermined intervals set by selector 36, or upon demand by pressing a pushbutton 34, timer 32 initiates a pulse rate mode by activating switch 28 to transfer speaker 24 to the output from microcomputer controller 38. Timer 32 also initiates a pulse rate measurement program stored in the permanent memory or ROM of controller 38. A series of electrical pulses are sent to the IR source 48, which converts them to IR radiant energy pulses at a rate sufficient to sample the variations in blood flow through the inner ear. The inner ear tissues reflect varying IR energy response levels to sensor 50, where they are converted to an electrical pulse-rate signal , which is output on lead 52. The electrical pulse-rate signal is amplified in amplifier 54, and the amplified signal is transmitted to a pulse rate analyzer 42. Pulse rate analyzer 42 converts the pulse rate signal to a voice command signal comprising an encoded signal for generating a specific numerical pulse rate, such as "72".

Voice synthesizer 40 includes in its memory a table of preselected stored audio output signals corresponding to stored voice command signals, as well as a table of pre-stored phrases such as "your pulse rate is". The programming and storing of a table of command signals and corresponding audio responses for a voice synthesizer is well known to those skilled in the art. Microcontroller 38 receives a voice command signal from pulse rate analyzer 42 and transmits it to voice synthesizer 40, which returns a stored phrase and an audio signal corresponding to the specific numerical pulse rate, such as "your pulse rate is 72". This audio signal is transmitted to speaker 24 via switch 28. After the pulse rate has been communicated to the user, switch 28 is returned to its previous switched state by microcontroller 38 to allow the user to hear the audio entertainment signal from entertainment center 26.

The earpiece is connected to the headset by the conductor sheath 68. In wearing the monitor, the headset is first placed in position with the speaker in one ear. Then the earpiece is inserted so that the projecting portion enters the ear canal and the flexible cup is then rotated slightly until a comfortable fit is achieved.

By employing an earpiece 44 having a pulse rate detector with an infrared source/sensor pair operating in the reflective mode and adapted to fit into an ear canal, a much more reliable and accurate pulse rate signal is received with less spurious noise than previously available from ECG electrodes or from IR devices which are externally attached to body portions.

While there has been shown what is considered to be the preferred embodiment of the invention, other modifications will occur to those skilled in the art, and it is desired to secure in the appended claims all such modifications as fall within the true spirit and scope of the invention.

What is claimed is:

1. An improved heartbeat monitor for wearing by a user during exercise, said monitor being of the type comprising a microcomputer controller, a pulse rate analyzer connected to receive an electrical pulse-rate signal and to output a voice command signal corresponding to a heartbeat rate of the user, a voice synthesizer providing a plurality of stored audio output signals corresponding to values assigned to a plurality of stored voice command signals, said microcomputer controller being programmed to receive a voice command signal from the pulse rate analyzer, to supply said voice command signal to the voice synthesizer, and to output an audio signal corresponding to the pulse rate, and a headset having speaker means adapted to be held in proximity to at least one ear of said user and connected to receive said output audio signal, whereby a voice message indicating heartbeat rate may be selectively heard through the user's speaker means, wherein the improvement comprises a pulse rate detector having an infrared source and an infrared sensor comprising a source/sensor pair adapted to fit into an ear canal of said user and arranged and oriented to operate in the reflective mode, said infrared source being operatively connected to said microcomputer controller and cooperating with said infrared sensor to provide an electrical pulse-rate signal responsive to said user's heartbeat rate, and wherein said pulse rate detector includes an earpiece adapted to fit inside the outer ear of the user, the earpiece including a projecting portion adapted to fit within the ear canal, said source/sensor pair being disposed on the end of the projecting portion and directed into the ear canal so as to illuminate the ear canal and cause IR radiation from the source to be variably reflected from the ear canal tissue to the sensor.

2. The combination according to claim 1, wherein the headset is adapted to hold the speaker means in at least one ear and wherein the earpiece comprises a flexible cup arranged to be supported by portions of the outer ear.

3. The combination according to claim 2, wherein the flexible cup includes a tab arranged to assist the user in withdrawing the projecting portion from the ear canal.

4. The combination according to claim 1, wherein the headset is adapted to hold the speaker means in at least one ear and also adapted to hold the earpiece in one ear.

5. The combination according to claim 4, wherein the earpiece is attached to and held in the ear canal by said headset.

\* \* \* \* \*